United States Patent [19]

Timár et al.

[11] Patent Number: 4,716,238

[45] Date of Patent: Dec. 29, 1987

[54] CHROMENE DERIVATIVES USEFUL AS INSECTICIDES

[75] Inventors: Tibor Timár; Kálmán Zsupán; János Répási; Irén Borsos née Safranek, all of Tiszavasvári; István Kiss, Szeged; Amdrás Fodor, Szeged; Péter Maróy, Szeged, all of Hungary

[73] Assignee: Alkaloida Vegyeszeti Gyar, Tiszavasvári, Hungary

[21] Appl. No.: 580,097

[22] Filed: Feb. 14, 1984

[30] Foreign Application Priority Data

Feb. 15, 1983 [HU] Hungary ........................... 504

[51] Int. Cl.$^4$ .......................................... C07D 311/58
[52] U.S. Cl. ............................................... 549/408
[58] Field of Search ........................ 549/408; 514/456

[56] References Cited

U.S. PATENT DOCUMENTS

| 2,354,492 | 7/1944 | Adams | 549/408 |
| 4,162,326 | 7/1979 | Mihailovski | 549/408 |
| 4,323,505 | 4/1982 | Hashimoto et al. | 549/408 |
| 4,542,150 | 9/1985 | Bowers | 514/456 |

FOREIGN PATENT DOCUMENTS

| 0040637 | 3/1980 | Japan | 549/408 |
| 0109779 | 7/1982 | Japan | 549/408 |
| 7513616 | 11/1975 | Netherlands | 549/408 |
| 0213149 | 5/1941 | Switzerland | 549/408 |

OTHER PUBLICATIONS

Chatterjea et al., Indian Journ. Chem., 12 (Dec. 1974), pp. 1256–1258.

*Primary Examiner*—Nicky Chan
*Attorney, Agent, or Firm*—Karl F. Ross; Herbert Dubno; Jonathan Myers

[57] ABSTRACT

The invention relates to pesticidal compositions comprising as active ingredient a compound of the general Formula I

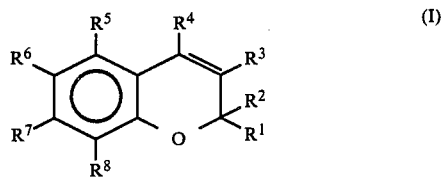

wherein
$R^1$ and $R^2$ stand for hydrogen, optionally halogenosubstituted $C_{1-6}$ alkyl or aryl;
$R^3$ and $R^4$ are hydrogen, halogen or $C_{1-6}$ alkyl;
$R^5$, $R^6$, $R^7$ and $R^8$ are hydrogen, hydroxy, mercapto, amino, $C_{1-10}$ alkyl; a group containing a methoxy, ethoxy, n-propoxy, isopropoxy, n-butoxy, sec. butoxy, isobutoxy, tert. butoxy, n-pentyloxy, cyclopropyloxy, cyclobutyloxy, cyclopentyloxy, cyclohexyloxy, cycloheptyloxy, cyclooctyloxy, allyloxy, crotyloxy, prenyloxy, propargyloxy, substituted propargyloxy, $C_{1-3}$ alkylenedioxy, aralkoxy, substituted aralkoxy, hydroxyalkoxy, alkoxyalkoxy, mercaptoalkoxyalkoxy, halogenoalkoxy, dihalogenoalkoxy, trihalogenoalkoxy, polyhalogenoalkoxy, N,N-dialkylaminoalkoxy, cycloalkylaminoalkoxy, alkylenoxyalkyleneoxy, alkylene-thia-alkylenoxy or alkylene-aza-alkylenoxy unit or $C_{2-6}$ acyl or a salt thereof and to a process for the preparation of the active ingredient.

1 Claim, No Drawings

CHROMENE DERIVATIVES USEFUL AS INSECTICIDES

FIELD OF THE INVENTION

This invention relates to chromene derivatives, a process for the preparation thereof and pesticidal compositions containing same.

BACKGROUND OF THE INVENTION

The so-called Precocene-1 (P1) and Precocene-2 (P2) are known substances isolated from natural sources. Bowers et al reported on the biological effects of P1 and P2 [W. S. Bowers, T. Ohta et al: Science 193, 542 (1976)]. On the basis of this biological activity it could be expected that P1 and P2 would be useful as new-type pesticide causing no environmental pollution.

Several articles have been published on the biological activity, mechanism of action and metabolism of precocenes. It is known that these compounds exert their action by damaging the juvenile hormone producing organ of insects, i.e. by special injury of the so-called "corpora allata". On testing the effects of the substances isolated from nature the correlation between the given biological group of effects and the 2H-chromene ring-system has been studied. According to experimental results the character and strength of the activity of precocenes depends to a large extent on the pest species, the test method used and from the point of view of chemical structure probably on the number and position of the substituents of the aromatic ring, the strength of the double bond of the pyrane ring and on the electronic and steric parameters of the complete molecule; [W. S. Bowers, R. Paro Martinez: Science 197 1369 (1977); H. Schooneveld: Experientia 35 363 (1979); W. S. Bowers: Pontif. Acad. Sci. Scr. Varia 41 129 (1976); G. T. Brooks et al: Nature 281 570 (1979); T. Ohta: Kagaku to Seibutsu 17(2) 92 (1979); T. Ohta: Konchu no Seiri to Kagaku 63 (1979); G. Matolcsy et al: Z. Naturforsch. 35b. 1449 (1980); G. T. Brooks et al: Proc. Br. Crop. Prot. Conf. Pests. Dis. 1 273 (1979); G. E. Pratt et al: Nature 284 320 (1980; D. M. Soderlund et al: J. Agr. Food Chem. 28(4) 724 (1980) D. A. Schooley et al: Pestic. Biochem. Physiol. 13(2) 95 (1980); A. P. Ottridge et al: Pestic Sci. 12(3) 245 (1981). Sci. Papers of the Inst. of Org. and Phys. Chem. of Wroclaw Techn. Univ. No. 22(7) 309–424 (1981); G. E. Pratt; G. T. Brooks ed. Juvenile Hormon Biochemistry. Elsevier/North-Holland Biomed Press 311–437 (1981)].

As a result of the above research work derivatives considerably more active than natural P1 and P2 were prepared, e.g. 6-methoxy-7-ethoxy-2,2-dimethyl-2H-chromene (P3, ZR 3623) and 6-methoxy-7-isopropoxy-2,2-dimethyl-chromene.

According to prior art [CHROMANES, CHROMANONES AND CHROMONES G. P. Ellis Ed.,: John Wiley and Sons, London, pages 43–66, (1977)] 2H-chromenes can be prepared by several synthesis routes relatively independent from each other and generally these methods are used for the preparation of synthetic precocenes.

According to patent literature the corresponding analogues are obtained by similar methods (German Federal Republic Pat. No. 2,639,671, U.S. Pat. No. 4,162,326, Japanese Pat. Nos. 73121/79, 15411/80, 40637/80 and 43039/80, Spanish Pat. Nos. 496,301 and 496,302).

However the number of precocene analogues disclosed in available patent literature is rather low.

DISCLOSURE OF THE INVENTION

The new compounds of the present invention are analogues of Precocene-1 (P1) and Precocene-2 (P2) isolated in nature.

According to an aspect of the present invention there are provided new chromene derivatives of the Formula I

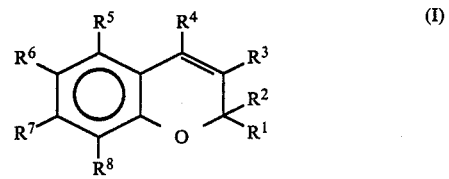

and salts thereof wherein $R^1$ and $R^2$ are hydrogen, unsubstituted or substituted halogenosubstituted $C_{1-6}$ alkyl or aryl;

$R^3$ and $R^4$ are hydrogen, halogen or $C_{1-6}$ alkyl;

$R^5$, $R^6$, $R^7$ and $R^8$ are hydrogen, hydroxy, mercapto, amino, $C_{1-10}$ alkyl; a group containing a methoxy, ethoxy, n-propoxy, isopropoxy, n-butoxy, sec. butoxy, isobutoxy, tert. butoxy, n-pentyloxy, cyclopropyloxy, cyclobutyloxy, cyclopentyloxy, cyclohexyloxy, cycloheptyloxy, cyclooctyloxy, allyloxy, crotyloxy, prenyloxy, propargyloxy, substituted propargyloxy, $C_{1-3}$ alkylenedioxy, aralkoxy, substituted aralkoxy, hydroxyalkoxy, alkoxyalkoxy, mercaptoalkoxyalkoxy, halogenoalkoxy, dihalogenoalkoxy, trihalogenoalkoxy, polyhalogenoalkoxy, N,N-dialkylaminoalkoxy, cycloalkylaminoalkoxy, alkylenoxyalkyleneoxy, alkylene-thia-alkylenoxy or alkylene-aza-alkylenoxy unit or $C_{2-6}$ acyl and salts thereof.

According to a further aspect of the present invention there is provided a process for the preparation of new chromene derivatives of the Formula I and salts thereof which comprises for the preparation of compounds of the Formula IA

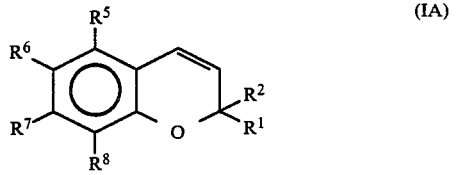

(a) dehydrating a chromanol derivative of the Formula III;

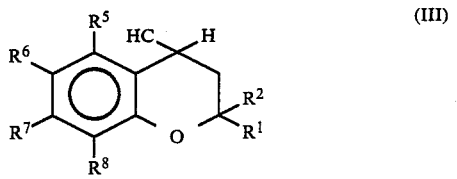

or (b) reacting a cumarine derivative of the Formula IV

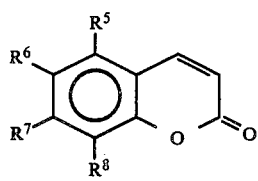 (IV)

with a Grignard compound of the general Formula $R^1MgX$ and/or $R^2MgX$; or (c) dehydrating a quinone-allyde of the Formula VI;

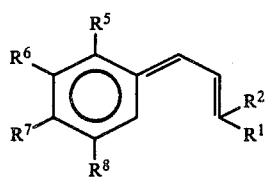 (VI)

or (d) dehydrohalogenating a chromane derivative of the Formula VII; or

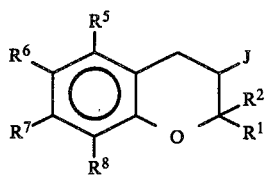 (VII)

(e) cyclizing an ether of the Formula X; or

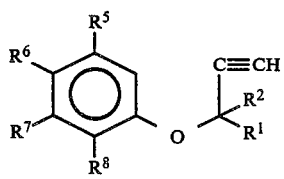 (X)

(f) reacting a phenol of the Formula VIII

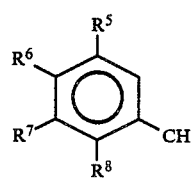 (VIII)

with a carbonyl derivative of Formula XI

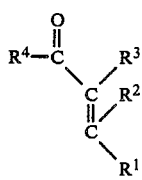 (XI)

or a protected derivative thereof; or (a) oxidizing a chromane derivative of the Formula XIII; or

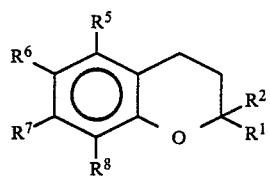 (XIII)

for the preparation of compounds of the Formula IB

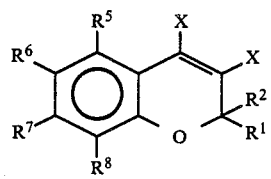 (IB)

(h) reacting a chromanone derivative of the Formula II

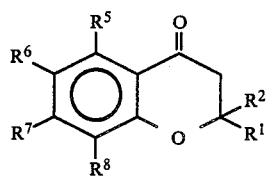 (II)

with a phosphorous pentahalide; and if desired converting a compound of the Formula I into a salt thereof or liberating a compound of the Formula I from its salt, (in which Formulae $R^1$, $R^2$, $R^3$, $R^4$, $R^5$, $R^6$, $R^7$ and $R^8$ have the same meaning as stated above and X stands for halogen).

According to a further feature of the present invention there are provided pesticidal compositions comprising as active ingredient at least one compound of the Formula I or a salt thereof in admixture with suitable inert carriers.

As already mentioned above only a few precocene analogues are disclosed in relevant publications.

It is the object of the present invention to provide a large number of new derivatives which enables the selection of more active compounds based on the correlation between biological effect and chemical structure.

According to our best knowledge the order of succession of the antijuvenile hormone activity of only 30–50 compounds is determined on one or two insect species. On the other hand there is very little available information on the so-called conventional "cid" effect, sterilizing, ovicidal and diapausa-inducing effect. In other terms we consider the following items of fundamental importance:

(a) Synthesis of new precocene analogues based on the correlation between chemical structure and biological effect known from relevant prior art. (b) Activity tests (AJH, sterilizing, ovicidal, diapausa-inducing, "cid-effect) on as many different pest species as possible.

(c) Determination of activity of various different formulations which effect the activity of the pure active ingredient.

(d) Extension of the tests on soil-dwelling nematodes in order to find so-called "nematocidal agents".

By using and modifying the synthetic methods suitable for the preparation of 2H-chromenes a number of new precocene derivatives are obtained. Several new compounds show valuable or even excellent activity on various test organisms.

The following processes are known per se for the preparation of other compounds:

(1) According to a variant of the process of the present invention the corresponding substituted 4-chromanone of the Formula II is reduced with a complex metal hydride or by catalytic hydrogenation. The 4-chromanol of the general Formula III thus obtained is dehydrated after or without isolation to yield the desired 2H-chromene of the general Formula I, T. Ohta; W. S. Bowers: Chem. Pharm. Bull. 25(9) 2788-9 (1977); M. Tsukayama et al: Heterocycles 16(6) 955 (1981); British patent 758,313 (1956); F. Baranton et al: Bull. Soc. Chim. Fr. 4203 (1968); CHROMENES, CHROMANONES AND CHROMONES, G. P. Ellis ed.; John Wiley and Sons; London 183. (1977).

(2) According to another variant of the process of the present invention a 4-chromanone of the Formula II is reacted with a phosphorous halide in the presence of a perhalogenated alkane as solvent. Thus 3,4-dihalogeno-2H-chromenes of the Formula I are obtained [F. Camps et al: Tetr. Lett. 40, 3901-2 (1979)].

(3) According to a further variant of the process of the present invention the 2H-chromenes of the Formula I are obtained by reacting the corresponding substituted cumarine derivative of the Formula IV with an alkyl (aryl) magnesium halide in anhydrous ether as medium and subjecting the reaction mixture to aqueous decomposition, R. L. Shriner; A. G. Sharp: J. Org. Chem. 4 575 (1939); L. I. Smith; P. M. Ruoff: J. Am. Chem. Soc. 62 145 (1940); H. P. Pommier et al: Can. J. Chem. 57(11) 1377 (1979).

(4) According to a further variant of the process of the present invention the corresponding substituted ortho-allyl-phenol of the Formula V

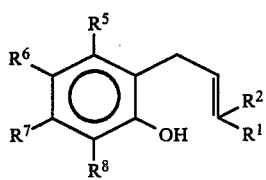

is subjected to oxidative cyclodehydration via the corresponding ortho-quinone-allyde of the Formula VI to yield the desired compound of the Formula I, G. Cardillo et al: J. Chem. Soc. Chem. Comm. 19 836 (1979); G. Casiraghi et al: Synthesis 4 310 (1981).

(5) According to a further variant of the process of the present invention a substituted ortho-allyl-phenol of the Formula V is converted into a 3-iodo-chromane derivative of the Formula VII which is transformed into the 2H-chromene of the Formula I by alkaline dehydrohalogenation, A. Bongini et al: Tetr. Lett. 37 2545 (1979); L. Jurd; G. D. Manners: Synthesis 6 618 (1980).

(6) According to a further variant of the process of the present invention a phenol of the Formula VIII is reacted with an acetylene derivative of the Formula IX

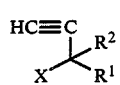

and the aryl propargyl ether of the Formula X, thus obtained is cyclized into the desired 2H-chromene derivative of the general Formula I, J. Hlubucek; E. Ritchie; W. C. Taylor: Aust. J. Chem. 11 2347 (1971); D. J. Gale; J. F. K. Wilshire: J. Text. Inst. 12 525 (1979); R. Chenevert et al: Experientia 36 379 (1980).

(7) According to a further variant of the process of the present invention the corresponding substituted phenol of the Formula VIII is reacted with a $\alpha,\beta$-unsaturated carbonyl compound of the Formula XI, to yield a 2H-chromene of the Formula I [G. Sartori et al: J. Org. Chem. 44, (5) (1979)].

(8) According to a further variant of the process of the present invention a substituted phenol of the Formula VIII is reacted with a dihalogeno compound of the Formula XII

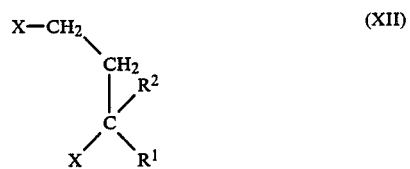

and the chromane derivative of the Formula XIII is oxidized into the desired 2H-chromene of the general Formula I, [F. Camps et al: Synthesis 2 126 (1979); A. C. Jain:, Zutschi; M. K.: Tetr. Lett. 3179 (1971)].

(9) According to a further variant of the process of the present invention the corresponding substituted phenol of the Formula VIII is reacted with a diene of the Formula XIV

and the chromane of the Formula XIII, thus obtained is oxidized into the desired 2H-chromene of the Formula [I, I. Noriyuki; et al: Japanese patent No. 43039/80; W. K. Ahluwalia et al: Synthesis 526 (1981); L. Bolzoni et al: Angew. Chem. Int. Ed. Engl. 17(9) 864 (1978)].

(10) According to a further variant of the process of the present invention a substituted phenol of the Formula VIII is reacted with a substituted allyl halide of the Formula XV

and the chromane of the Formula XIII, thus obtained is oxidized into the desired 2H-chromene derivative of the general Formula I [S. Yamada et al: J.Chem. Soc. Jap. Chem. Ind. Chem. 7, 1192-4 (1981)].

(11) According to a further variant of the process of the present invention a substituted ortho-hydroxy-acetophenone of the Formula XVI

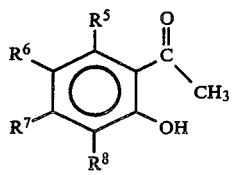 (XVI)

is reacted with a ketone of the Formula XVII,

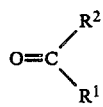 (XVII)

the compound of the Formula XVIII

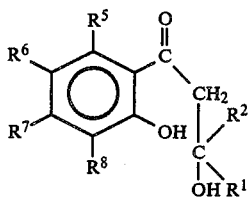 (XVIII)

is subjected to acidic cyclication and the 4-chromanone of the Formula II, thus obtained is converted into the desired 2H-chromene derivative of the Formula I in accordance with the first variant of the process [A. Banerji: N. C. Goomer: Ind. J. Chem. 20B 144–6 (1981); A Banerji: J. of Lab. Comp. and Radiopharm. 18 (12) 1737 (1981); F. Bohlmann et al: Chem. Ber. 114 147 (1981); A. Banerji et al: Synth. Comm. 10(11) 851 (1980); A Banerji et al: Tetr. Lett. 38 3685 (1979)].

The preferred reaction conditions and modes for carrying out the variants of the process of the present invention are disclosed below. In the Formulae $R^1$–$R^8$ and X have the same meaning as stated above.

(a) A 4-chromanone derivative of the Formula II is subjected to reduction with a complex metal hydride or catalytical hydrogenation or to Meerwein-Ponndorf reduction and the 4-chromanol of the Formula III, thus obtained is dehydrated with the aid of a dehydrating agent.

(b) A 4-chromanone of the Formula II is reacted with a phosphorous halide in a perhalogenated alkane as solvent.

(c) A cumarine derivative of the Formula IV is reacted with a Grighard reagent of the Formula $R^1MgX$ and/or $R^2MgX$ (where X is halogen).

(d) A substituted ortho-allyl phenol of the Formula V is subjected to cyclodehydration via an ortho-quinone-allyde of the Formula VI.

(e) A substituted ortho-allyl phenol of the formula V is converted into a iodo-chromane of the Formula VII and the product thus obtained is dehydrohalogenated in alkaline medium.

(f) A phenol of the Formula VIII is reacted with an acetylene derivative of the Formula IX in the presence of a base and an alkali iodide catalyst, in a bipolar-aprotic solvent and the aryl-propargyl ether thus obtained is cyclised in a N,N-dialkyl aryl amine.

(g) A phenol of the Formula VIII is reacted with an α,β-unsaturated carbonyl compound of the Formula XI in an aromatic aprotic solvent.

(h) A phenol of the Formula VIII is reacted with a dihalogeno alkane of the Formula XII whereupon the chromane derivative of the Formula XIII thus obtained is oxidized.

(i) A phenol of the Formula VIII is reacted with a diene of the Formula XIV and the chromane derivative of the Formula XIII thus obtained is oxidized.

(j) A phenol of the formula VIII is reacted with a substituted allyl halide of the Formula XV and the chromane derivative of the Formula XIII thus obtained is oxidized.

(k) An ortho-hydroxy-acetophenone of the Formula XVI is reacted with a ketone of the Formula XVII, the compound of the Formula XVIII thus obtained is subjected to acidic cyclization and the 4-chromanone derivative of the Formula II thus obtained is converted into the desired 2H-chromene derivative of the Formula I according to process 1.

The compounds of the Formula I can be used in pesticidal compositions. The said pesticidal composition comprises as active ingredient a compound of the Formula I or a salt thereof as active ingredient in admixture with a suitable carrier.

The pesticidal compositions may comprise inert solid or liquid diluents or carriers and further additives (e.g. wetting, emulsifying, dispersing agents and/or surfactants.) The additives may be those generally used in the field of pesticides. The compositions may be prepared by methods known per se.

TECHNICAL FIELD OF APPLICATION

The new compounds of the present invention are valuable pesticides, particularly insecticides which can be readily used in agriculture and horticulture.

MODES OF EMBODIMENT OF THE INVENTION

Further details of the present invention are to be found in the following Examples without limiting the scope of protection to the said Examples.

The purity of the compounds prepared according to the Examples is controlled by thin layer chromatography and gas chromatography. The chemical structure of the compounds is confirmed by IR, NMR and MS spectrum.

The NMR spectra are disclosed as follows: e.g. 1.45 (3H, t; J=5 Hz), wherein 1.45=chemical shift;
3H=number of protons belonging to this said sign;
t=multiplicity of the sign;
J=coupling constant;
multiplet designations:
s=singulet
d=doublet
t=triplet
q=quartet
m=multiplet of higher order
sz=broad protracted sign.

EXAMPLE 1

Preparation of 6,7-dibenzyloxy-2,2-dimethyl-2H-chromene 7.8 g (20 millimoles) of 6,7-dibenzyloxy-2,2-dimethyl-4-chromanone are dissolved in 100 ml of a 1:1 mixture of tetrahydrofurane and water, whereupon 5.3 g (30 millimole) of palladium chloride and 8.31 g (220 millimoles) of sodium tetrahydroborate are added. The reaction mixture is stirred at 0° C. for 3 hours, filtered, and the filtrate is extracted three times with 100 ml of ether each. The ether extracts are evaporated, the residue is dissolved in 300 ml of dichloro methane and allowed to stand at 35° C. in the presence of 15 ml of pyridine and 2 g of phosphorous oxychloride for an hour. The reaction mixture is poured into 100 ml of water washed with 5% hydrochloric acid and water. The organic phase is dried and evaporated. The residue is crystallized from methanol. Thus 6 g of the desired compound are obtained, yield 81%. Mp.: 50°–51° C.

EXAMPLE 2

Preparation of 3,4-dichloro-6-methoxy-7-isopropoxy-2,2-dimethyl-2H-chromene

A suspension of 2.64 g (10 millimoles) of 6-methoxy-7-isopropoxy-2,2-dimethyl-4-chromanone, 4.2 g (20 millimoles) of phosphorous pentachloride and 30 ml of carbon tetrachloride is stirred at 30° C. for 8 hours. The reaction mixture is evaporated and the residue is purified by crystallization from ethanol. Thus 3.8 g of the desired compound are obtained. Yield 60%. Mp.: 80°–85° C.

EXAMPLE 3

Preparation of '7-n-pentyloxy-2,2,5-trimethyl-2H-chromene 4.6 g (20 millimoles) of 5-methyl-7-n-pentyloxy-cumarine are dissolved in 70 ml of anhydrous ether and the solution thus obtained is added to an etheral solution of 100 ml of methyl magnesium iodide (prepared from 1.5 g of magnesium and 8.5 g of methyl iodide) under stirring. The reaction mixture is heated to boiling for 5 hours, under stirring, allowed to stand overnight and decomposed by adding 200 ml of a 5% ammonium chloride solution. The reaction mixture is worked up in the usual manner and purified by column chromatography (adsorbent: Kieselgel-60: eluent: a 9:1 mixture of hexane and ether). Thus 3.8 g of the desired compound are obtained in the form of a colorless oil, yield 74%.

EXAMPLE 4

Preparation of 7-isobutoxy-8-methoxy-2,2-dimethyl-2H-chromene

A mixture of 5.8 g (22 millimoles) of 2-prenyl-5-isobutoxy-6-methoxy-phenol, a molar equivalent amount of methyl-trialkyl ($C_8$–$C_{10}$)-ammonium dichromane and 100 ml of benzene is refluxed for 10 hours. The reaction mixture is diluted with hexane, washed with 20% sodium thiosulfate, the organic phase is dried, evaporated and the residue is purified by column chromatography (see Example 3). Thus 4.6 g of the desired compound are obtained in the form of a colorless oil, yield 80%.

EXAMPLE 5

Preparation of 5-methoxy-8-sec.butoxy-2,2-dimethyl-2H-chromene 5.8 g (22 millimoles) of 2-prenyl-3-methoxy-5-sec.-butoxy-phenol are dissolved in 100 ml of dichloro methane, whereupon 5 g (22 millimoles) of N-iodo-succinimide are added. The reaction mixture is stirred at 30° C. for 1 hour, diluted with 200 ml of water, the organic phase is separated washed with a 5% sodium thiosulfate solution, dried and evaporated. The residue is dissolved in 100 ml of a 10% methanolic sodium hydroxide solution and allowed to stand at 50° C. for 2 hours. The solution is diluted with water and extracted with ether. The organic phase is washed subsequently with a 1% hydrochloric acid solution and water, the solvent is removed and the product purified as described in Example 3. Thus 5.5 g of the desired compound are obtained in the form of a light yellow oil. Yield: 95%.

EXAMPLE 6

Preparation of 7-n-propoxy-8-methoxy-2,2-dimethyl-2H-chromene

A suspension of 5.5 g (30 millimoles) of 2-methoxy-3-n-propoxy-phenol, 6.5 g (60 millimoles) of 3-chloro-3-methyl-but-1-ine, 5 g of potassium carbonate, 8 g of potassium iodide and 50 ml of anhydrous acetone is heated to boiling under stirring for 20 hours. The inorganic salt is filtered off, the filtrate evaporated and the residue heated to boiling in 100 ml of N,N-dimethyl aniline for 8 hours. The reaction mixture is worked up in the usual manner and the product is purified as described in Example 3. Thus 5.9 g of the title compound are obtained in the form of a colorless oil, yield 80%.

EXAMPLE 7

Preparation of 7-ethoxy-2,2,8-trimethyl-2H-chromene

To a solution of 5.7 g (25 millimoles) of titanium tetraethoxide in 50 ml of toluene a solution of 13.8 g (100 millimoles) of 2-methyl-3-ethoxy-phenol and 50 ml of toluene is added at 20° C. under nitrogen. The orangered solution is heated to boiling for an hour, and subjected to slow distillation until the ethanol is removed. The mixture is cooled to room temperature and a mixture of 10.6 g (150 millimoles) of dimethyl acroleine and 200 ml of toluene is added dropwise. The reaction mixture is heated to boiling for 8 hours, diluted with a saturated ammonium chloride solution and extracted with ether. The solvent is removed and the residue purified as described in Example 3. This 10.2 g of the desired compound are obtained in the form of a colorless oil, yield 50%.

EXAMPLE 8

Preparation of 5-methoxy-7-isobutoxy-2,2-dimethyl-2H-chromene

A mixture of 3.9 g (20 millimoles) of 3-methoxy-5-isobutoxy-phenol, 2.8 g (20 millimoles) of 1,3-dichloro-3-methyl-butane and 0.26 g (1 millimole) of bis-(acetyl-acetonato)-nickel is heated at 125° C. for 8 hours. The mixture is cooled, the solvent removed, the residue taken up in 40 ml of anhydrous benzene and 0.8 g (3.5 millimoles) of DDQ (dichloro-dicyano-benzoquinone) are added. The mixture is heated to boiling for 60 hours. The solution is filtered, the filtrate evaporated and the residue purified as described in Example 3. Thus 3.6 of the desired compound are obtained in the form of a colorless oil, yield 69%.

EXAMPLE 9

Preparation of 7-methoxymethoxy-2,2-dimethyl-2H-chromene 7.7 g (50 millimoles) of 3-methoxymethoxy-phenol and 110 g of 50% sulfuric acid are dissolved in 150 g of chloroform, whereupon 6.8 g of isoprene are added at 60° C. within 20 minutes. The reaction mixture is allowed to stated at 60° C. for 3 hours, separated, the organic phase is evaporated and the residue is heated to boiling in the presence of 2.5 g of dichloro-dicyano-benzoquinone in 100 ml of dioxane for 10 hours. Then one proceeds as described in Example 8. Thus 7.6 g of the desired compound are obtained in the form of a light yellow oil, yield 69%.

EXAMPLE 10

Preparation of 7-isopropoxy-8-methoxy-2,2-dimethyl-2H-chromene 5.5 g (30 millimoles) of 2-methoxy-3-isopropoxy-phenol are dissolved in 30 ml of ether whereupon 2.1 g of metallic sodium are added in small portions and the mixture is heated to boiling for an hour. To the mixture 3.2 g (30 millimoles) of prenyl chloride are added dropwise and the reaction mixture is heated to boiling for 8 hours. The reaction mixture is worked up in the usual manner. Thus 4.4 g of "chromane" are obtained. This product is dissolved in 60 ml of benzene, 1.2 g of dichloro-dicyano-benzoquinone are added and the reaction mixture is purified as described in Example 3. Thus 3.7 g of the desired compound are obtained in the form of a colorless oil, yield 50%.

EXAMPLE 11

Preparation of 7-sec.butoxy-8-methoxy-2,2-dimethyl-2H-chromene

To a solution of 2.2 millimoles of lithium diisopropyl amide and 50 ml of anhydrous tetrahydrofurane at −30° C. a solution of 2 g (8.4 millimoles) of 2-hydroxy-3-methoxy-4-sec.butoxy-acetophenone in 10 ml of tetrahydrofurane is added dropwise. The reaction mixture is stirred for an hour, cooled to −40° C., 10 millimoles of acetone are added. The mixture is stirred for 2 hours, diluted with ether, acidified, the organic layer is removed and the residue dissolved in 100 ml of methanol. The mixture is heated to boiling in the presence of 10 ml of concentrated hydrochloric acid for 7 hours and poured onto 200 g crushed ice. The crystalline substance is filtered, dried and worked up as described in Example 1. The product is purified according to Example 3. Thus 1.3 g of the desired compound are obtained in the form of a colorless oil. Yield 59%.

The compounds enumerated in Table I are prepared by the methods according to preceding Examples.

TABLE I

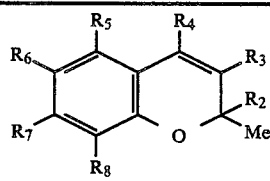

| No. | $R_2$ | $R_3$ | $R_4$ | $R_5$ | $R_6$ | $R_7$ | $R_8$ | Example No. | Yield /%/ |
|---|---|---|---|---|---|---|---|---|---|
| 1 | Me | H | H | H | H | nPrO | H | 3 | 72 |
| 2 | Me | H | H | H | H | iPrO | H | 3 | 69 |
| 3 | Me | H | H | H | H | iBuO | H | 3 | 64 |
| 4 | Me | H | H | H | H | c-pentyl O | H | 3 | 62 |
| 5 | Me | H | H | H | H | c-hexyl O | H | 3 | 59 |
| 6 | Me | H | H | H | H | MeOCH$_2$O | H | 9 | 69 |
| 7 | Me | H | H | H | H | MeSCH$_2$O | H | 4 | 76 |
| 8 | Me | H | H | H | H | EtOCH$_2$O | H | 4 | 69 |
| 9 | Me | H | H | H | H | crotyl O | H | 1 | 76 |
| 10 | Me | H | H | H | H | prenyl O | H | 1 | 82 |
| 11 | Me | H | H | H | H | benzyl O | H | 5 | 89 |
| 12 | Me | H | H | H | H | HO—n-butyl O | H | 1 | 72 |
| 13 | Me | H | H | H | H | Me$_2$N—/CH$_2$/$_2$O | H | 8 | 57 |
| 14 | Me | H | H | H | H | pyrrolidino—/CH$_2$/$_2$O | H | 8 | 61 |
| 15 | Me | H | H | H | H | piperidino—/CH$_2$/$_2$O | H | 8 | 49 |
| 16 | Me | H | H | H | H | morpholino—/CH$_2$/$_2$O | H | 8 | 63 |
| 17 | Me | H | H | Me | H | EtO | H | 6 | 75 |
| 18 | Me | H | H | Me | H | nPrO | H | 6 | 71 |
| 19 | Me | H | H | Me | H | iPrO | H | 6 | 69 |
| 20 | Me | H | H | Me | H | sec BuO | H | 6 | 81 |
| 21 | Me | H | H | Me | H | iBuO | H | 6 | 73 |

TABLE I-continued

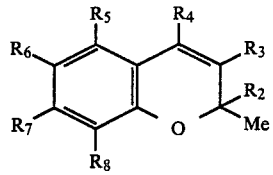

| No. | R₂ | R₃ | R₄ | R₅ | R₆ | R₇ | R₈ | Example No. | Yield /%/ |
|---|---|---|---|---|---|---|---|---|---|
| 22 | Me | H | H | Me | H | c-pentyl O | H | 3 | 74 |
| 23 | Me | H | H | Me | H | c-hexyl O | H | 9 | 69 |
| 24 | Me | H | H | Me | H | MeOCH₂O | H | 10 | 46 |
| 25 | Me | H | H | Me | H | MeSCH₂O | H | 10 | 49 |
| 26 | Me | H | H | Me | H | EtOCH₂O | H | 10 | 53 |
| 27 | Me | H | H | Me | H | allyl O | H | 1 | 76 |
| 28 | Me | H | H | Me | H | crotyl O | H | 1 | 82 |
| 29 | Me | H | H | Me | H | prenyl O | H | 1 | 87 |
| 30 | Me | H | H | Me | H | CH≡C—CH₂O | H | 1 | 79 |
| 31 | Me | H | H | Me | H | benzyl O | H | 7 | 47 |
| 32 | Me | H | H | Me | H | Me₂N—(CH₂)₂O | H | 8 | 61 |
| 33 | Me | H | H | Me | H | pyrrolidinyl-(CH₂)₂O | H | 8 | 48 |
| 34 | Me | H | H | Me | H | piperidinyl-(CH₂)₂O | H | 8 | 57 |
| 35 | Me | H | H | Me | H | morpholinyl-(CH₂)₂O | H | 8 | 62 |
| 36 | Me | H | H | H | H | EtO | Me | 7 | 50 |
| 37 | Me | H | H | H | H | nPrO | Me | 4 | 69 |
| 38 | Me | H | H | H | H | iPrO | Me | 4 | 78 |
| 39 | Me | H | H | H | H | sec BuO | Me | 4 | 82 |
| 40 | Me | H | H | H | H | iBuO | Me | 4 | 80 |
| 41 | Me | H | H | H | H | c-pentyl O | Me | 5 | 89 |
| 42 | Me | H | H | H | H | c-hexyl O | Me | 5 | 79 |
| 43 | Me | H | H | H | H | MeOCH₂O— | Me | 9 | 66 |
| 44 | Me | H | H | H | H | MeS—CH₂O— | Me | 9 | 61 |
| 45 | Me | H | H | H | H | EtOCH₂O | Me | 4 | 76 |
| 46 | Me | H | H | H | H | allyl O | Me | 1 | 82 |
| 47 | Me | H | H | H | H | crotyl O | Me | 1 | 76 |
| 48 | Me | H | H | H | H | prenyl O | Me | 1 | 69 |
| 49 | Me | H | H | H | H | benzyl O | Me | 6 | 78 |
| 50 | Me | H | H | H | H | CH≡C—CH₂O | Me | 1 | 81 |
| 51 | Me | H | H | H | H | Me₂N—(CH₂)₂O | Me | 8 | 63 |
| 52 | Me | H | H | H | H | pyrrolidinyl-(CH₂)₂O | Me | 8 | 59 |
| 53 | Me | H | H | H | H | piperidinyl-(CH₂)₂O | Me | 8 | 65 |

TABLE I-continued

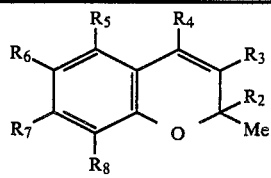

| No. | R$_2$ | R$_3$ | R$_4$ | R$_5$ | R$_6$ | R$_7$ | R$_8$ | Example No. | Yield /%/ |
|---|---|---|---|---|---|---|---|---|---|
| 54 | Me | H | H | H | H | O⌐N⌐CH$_2$CH$_2$O (morpholinoethoxy) | Me | 8 | 70 |
| 55 | Me | H | H | H | iBuO | iBuO | H | 11 | 47 |
| 56 | Me | H | H | H | benzyl O | benzyl O | H | 1 | 81 |
| 57 | Me | H | H | H | CF$_3$CH$_2$O | CF$_3$CH$_2$O | H | 1 | 61 |
| 58 | Me | H | H | H | allyl O | allyl O | H | 1 | 82 |
| 59 | Me | H | H | H | crotyl O | crotyl O | H | 1 | 69 |
| 60 | Me | H | H | H | prenyl O | prenyl O | H | 1 | 72 |
| 61 | Me | H | H | H | CH≡C—CH$_2$O | CH≡C—CH$_2$O | H | 1 | 80 |
| 62 | Me | Cl | Cl | H | EtO | EtO | H | 2 | 58 |
| 63 | Me | Cl | Cl | H | iPrO | iPrO | H | 2 | 62 |
| 64 | Me | Cl | Cl | H | MeO | EtO | H | 2 | 57 |
| 65 | Me | Cl | Cl | H | MeO | iPrO | H | 2 | 60 |
| 66 | Me | H | H | H | MeO | sec BuO | H | 5 | 76 |
| 67 | Me | H | H | H | MeO | iBuO | H | 5 | 84 |
| 68 | Me | H | H | H | MeO | c-pentyl O | H | 5 | 79 |
| 69 | Me | H | H | H | MeO | c-hexyl O | H | 5 | 83 |
| 70 | Me | H | H | H | MeO | benzyl O | H | 5 | 90 |
| 71 | Me | H | H | H | O—/CH$_3$/$_2$C—O | | H | 11 | 47 |
| 72 | Me | H | H | H | MeO | crotyl O | H | 1 | 69 |
| 73 | Me | H | H | H | MeO | prenyl O | H | 1 | 74 |
| 74 | Me | H | H | H | O—/CH$_2$/$_3$—O | | H | 10 | 47 |
| 75 | Me | H | H | H | MeO | MeOCH$_2$O | H | 4 | 76 |
| 76 | Me | H | H | H | MeO | MeSCH$_2$O | H | 4 | 59 |
| 77 | Me | H | H | H | H | EtO | EtO | 7 | 46 |
| 78 | Me | H | H | H | H | nPrO | nPrO | 7 | 49 |
| 79 | Me | H | H | H | H | iPrO | iPrO | 7 | 52 |
| 80 | Me | H | H | H | H | sec-BuO | sec-BuO | 7 | 51 |
| 81 | Me | H | H | H | H | iBuO | iBuO | 7 | 49 |
| 82 | Me | H | H | H | H | O—CH$_2$—O | | 9 | 63 |
| 83 | Me | H | H | H | H | O—/CH$_2$/$_2$—O | | 9 | 61 |
| 84 | Me | H | H | H | H | O—/CH$_2$/$_3$—O | | 9 | 69 |
| 85 | Me | H | H | H | H | O—/CH$_2$/$_2$—O—/CH$_2$/$_2$—O | | 9 | 48 |
| 86 | Me | H | H | H | H | benzyl O | benzyl O | 11 | 53 |
| 87 | Me | H | H | H | H | EtO | MeO | 11 | 49 |
| 88 | Me | H | H | H | H | nPrO | MeO | 6 | 80 |
| 89 | Me | H | H | H | H | sec-BuO | MeO | 11 | 59 |
| 90 | Me | H | H | H | H | iPrO | MeO | 10 | 50 |
| 91 | Me | H | H | H | H | iBuO | MeO | 4 | 80 |
| 92 | Me | H | H | H | H | c-pentyl O | MeO | 10 | 52 |
| 93 | Me | Cl | Cl | H | H | MeO | MeO | 2 | 57 |
| 94 | Me | Cl | Cl | H | H | EtO | MeO | 2 | 61 |
| 95 | Me | Cl | Cl | H | H | iPrO | MeO | 2 | 49 |
| 96 | Me | Cl | Cl | H | H | sec-BuO | MeO | 2 | 63 |
| 97 | Me | Cl | Cl | H | H | iBuO | MeO | 2 | 56 |
| 98 | Me | Cl | Cl | H | H | c-pentyl O | MeO | 2 | 51 |
| 99 | Me | H | H | EtO | H | EtO | H | 11 | 47 |
| 100 | Me | H | H | nPrO | H | nPrO | H | 11 | 51 |
| 101 | Me | H | H | iPrO | H | iPrO | H | 11 | 56 |
| 102 | Me | H | H | sec-BuO | H | sec-BuO | H | 11 | 61 |
| 103 | Me | H | H | iBuO | H | iBuO | H | 8 | 63 |
| 104 | Me | H | H | c-pentyl O | H | c-pentyl O | H | 8 | 67 |
| 105 | Me | H | H | benzyl O | H | benzyl O | H | 8 | 59 |
| 106 | Me | H | H | MeO | H | EtO | H | 8 | 57 |
| 107 | Me | H | H | MeO | H | nPrO | H | 5 | 86 |
| 108 | Me | H | H | MeO | H | iPrO | H | 5 | 79 |
| 109 | Me | H | H | MeO | H | sec-BuO | H | 5 | 95 |
| 110 | Me | H | H | MeO | H | iBuO | H | 8 | 69 |
| 111 | Me | H | H | MeO | H | c-pentyl O | H | 11 | 53 |
| 112 | Me | Cl | Cl | MeO | H | MeO | H | 2 | 52 |
| 113 | Me | Cl | Cl | MeO | H | EtO | H | 2 | 61 |
| 114 | Me | Cl | Cl | MeO | H | iPrO | H | 2 | 67 |
| 115 | Me | Cl | Cl | MeO | H | sec-BuO | H | 2 | 49 |
| 116 | Me | Cl | Cl | MeO | H | iBuO | H | 2 | 53 |
| 117 | Me | Cl | Cl | MeO | H | c-pentyl O | H | 2 | 61 |
| 118 | Me | H | H | MeO | H | CH$_3$OCH$_2$O | H | 3 | 59 |
| 119 | Me | H | H | MeO | H | EtO—CH$_2$O | H | 3 | 56 |
| 120 | Me | H | H | MeO | H | CH$_3$SCH$_2$O | H | 3 | 51 |

TABLE I-continued

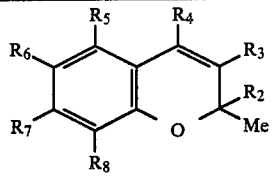

| No. | R$_2$ | R$_3$ | R$_4$ | R$_5$ | R$_6$ | R$_7$ | R$_8$ | Example No. | Yield /%/ |
|---|---|---|---|---|---|---|---|---|---|
| 121 | H | Me | H | H | H | MeO | H | 1 | 69 |
| 122 | H | Me | H | H | MeO | MeO | H | 1 | 73 |
| 123 | H | Me | H | H | H | MeO | MeO | 1 | 68 |
| 124 | H | Me | H | MeO | H | MeO | H | 1 | 49 |
| 125 | H | Me | H | H | MeO | EtO | H | 1 | 61 |
| 126 | H | Me | H | H | H | EtO | MeO | 1 | 72 |
| 127 | H | Me | H | MeO | H | EtO | H | 1 | 80 |
| 128 | H | Me | H | H | MeO | iPrO | H | 1 | 76 |

Determination of the effect of the precocene analogues according to Table I on the growth of insects and nematocidal test Test pests Insects:
- cotton bug (*Dysdercus fasciatus*)
- cabbage butterfly (*Pieris brassicae*)
- mustard beetle
- domestic fly (*Musca domestica*)
- pea plant-louse (*Acirtosypon pisi*)
- Colorado beetle Nematodes:
- *Caenorhabditis elegans*
- tomato root gall nematode (*Meloidogyne incognita*)

Preparation of 50 EC formulation of the active ingredient

| Component | Amount |
|---|---|
| Active ingredient of the Formula I | 500 g* |
| "Arylan" C.A. | 64.2 g |
| "Lubrol" N 13 | 40.0 g |
| Aromasol ad to | 1000.0 ml |

*calculated for 100% active ingredient

The tests are carried out by using spray obtained by aqueous dilution of the above emulsifiable concentrate.

The details of the tests used are disclosed below; the Colorado beetle test is completely identical with the cabbage butterfly test.

(1) Cotton bug test

A dilution series is prepared from the test compound with acetone, and 0.2 μl of each dilution is topically applied onto the back part of larvae of the II. stage of growth with the aid of a Hamiltion syringe. The active ingredient is absorbed through the cuticula. The animals are kept in a large glass and fed with cotton grains and water. After adult shedding the surviving insects are observed for eventual adultoid symptoms, the egg-reproduction and the development of the ovules is evaluated too.

(2) Cabbage butterfly

From the 50 EC of the test compound a dilution series is prepared with water and the host seedlings (cabbage) are sprayed with this composition until the spray runs down. The spray is allowed to dry whereupon 20 young larvae of the II. stage are placed on each treated plant and the seedlings are kept under so-called "long-day" illumination (18 hours of illumination and 6 hours of darkness). The nibbled plants are replaced by similarly sprayed plants if necessary. The killing rate of the insects, the growth rate of the larvae and the morphological deformations of the surviving nymphs and adults are registered.

(3) Mustard beetle

Two weeks old mustard seedlings are sprayed with a solution of 0.1 g of the test compound, 0.5 ml of dimethyl sulfoxide, and 10 μl of 50 EC composition in 10 ml of water. After the spray is dried, 20 mustard larvae of the II. stage are placed on each plant. The sprayed plants are changed every second day. The evaluation is based on the number of imagos hatching from the nymphs.

(4) Domestic fly

The fly larvae are grown on a nutrient medium of the following composition: 2 ml of milk; 2 ml of water; 2 g of wheat bran; 0.1 ml of saturated alcoholic nipagin solution.

The nutrient medium is filled into cylindrical glass vials (30×100 mm) and 25 fly larvae are raised in each vial. The test compound is dissolved in milk; the end concentration (related to milk) amounts to 0.1% which corresponds to 0.05% (related to the total nutrient medium). The solution of the active ingredient is admixed with the nutrient medium whereupon 25 ml of domestic fly larvae of the I. stage are placed into each vial and the vials are closed with a hard cotton-wool stopper. The nymphs emerging from the larvae are collected in each vial, counted and kept in a petri dish (diameter 25 mm) until flies hatch from the nymphs. The hatched flies are counted.

(5) *Caenorhabditis elegans*

0.5 ml of the acetonous solution of the test compound is applied onto a NGM agar plate free from bacteria in a Petri dish. After the acetone was dried 25–30 young adults are placed on the plate. After 24 hours the surviving and killed insects are counted.

(6) Root gall nematode

The test is carried out on II. stage infective larvae, which are collected from the root of tomato plant, placed on a filter and incubated in steril water at 25° C. The hatched larvae are collected every 24 hours and immidiately placed onto the treated nutrient medium. As nutrient medium NGM agar plate free from bacteria is used. 0.5 ml of the acetoneous solution of the test compound is applied onto the surface of the plate in a Petri-dish. After the acetone has evaporated 5 μl of the larva suspension is applied onto each plate. After 72 hours the surviving and killed insects are counted.

The test results are summarized in Tables II(1)–II(6). (Remark: in the cotton bug test 50 insects are used). In each Table the control value are disclosed too.

TABLE II(1)

Effect of the test compounds on cotton bug

| Test Compound Ia | $LD_{50}$ /μg/insect/ | AJH effect /μg/insect/ | Sterilizing effect /μg/insect/ |
|---|---|---|---|
| P2 | 0.6 | 1 | 10 |
| 60 | 0.6 | — | — |
| 66 | 0.4 | 0.1 | — |
| 67 | 0.4 | — | — |
| Control+ | — | — | — |

+on treating the animals with acetone the survival rate is 95%.

TABLE II(2)

Effect of the test compounds on cabbage butterfly

| Test compound Ia | Killing rate of larvae % | Survival nymph % | Survival adult % |
|---|---|---|---|
| P1 | 41 | 59 | 50 |
| 1 | 52 | 48 | 39 |
| 17 | 81 | 19 | 19 |
| 20 | 11 | 19 | 14 |
| 21 | 100 | — | — |
| 22 | 100 | — | — |
| 30 | 83 | 17 | 17 |
| 107 | 88 | 12 | 12 |
| 108 | 87 | 13 | 9 |
| 109 | 100 | — | — |
| 110 | 100 | — | — |
| 87 | 76 | 24 | 24 |
| 88 | 100 | — | — |
| 89 | 100 | — | — |
| 90 | 64 | 36 | 32 |
| 91 | 93 | 7 | 7 |
| Control+ | 12 | 88 | 88 |

+50 EC form but containing no active ingredient

In the 50 EC compositions P1 and test compound 1 are used in a concentration of 0.01%, and the other active ingredients in a concentration of 0.1%.

TABLE II(3)

Effect of the test compounds on mustard beetle

| Test compound Ia | Concentration | Survival of adults % |
|---|---|---|
| 21 | 1% | 27 |
| 88 | 1% | 45 |
| Control | 0% | 100 |

TABLE II(4)

Effect of test compounds on domestic fly

| Test compound Ia | Survival nymph /%/ | Survival adult /%/ |
|---|---|---|
| P1 | 100 | 33.3 |
| 3 | 100 | 28.2 |
| 17 | 40 | 14.8 |
| 19 | 50.9 | 27.6 |
| 20 | 25.4 | 12.5 |
| 21 | 45.7 | 25.5 |
| 22 | 52.7 | 31.8 |
| 30 | 50.9 | 10.6 |
| 107 | 9.1 | 6.4 |
| 110 | 0 | 0 |
| 87 | 5.4 | 4.2 |
| 88 | 12.7 | 0 |
| 90 | 12 | 0 |
| Control | 100 | 100 |

TABLE II(5)

Effect of test compounds on Colorado beetle

| Test compounds Ia | Developped imago /%/ |
|---|---|
| P2 | 68 |
| 56 | 0 |
| 91 | 21 |
| Control | 95 |

TABLE II(6)

Nematocidal effect of test compounds on Caenorhabditis elegans adult nematodes

| Test compound Ia | Concentration μg/ml | Lethality % | Size of descendant population | Remark |
|---|---|---|---|---|
| P1 | 200 | 44 | reduced | |
| | 400 | 98 | no descendants | |
| P2 | 200 | 100 | no descendants | |
| | 400 | 100 | no descendants | |
| P3 | 200 | 70 | some descendants | |
| | 400 | 90 | no descendants | |
| 30 | 200 | 20 | some descendants | paralysis |
| | 400 | 30 | no descendants | paralysis |
| 58 | 200 | 40 | some descendants | |
| | 400 | 90 | no descendants | |
| 87 | 200 | 40 | reduced | |
| | 400 | 100 | no descendants | |
| 90 | 200 | 60 | reduced | |
| | 400 | 73 | reduced | |
| 89 | 200 | 25 | reduced | |
| | 400 | 85 | reduced | |
| Control | — | 0 | normal | |
| 10% acetone | — | 0 | normal | |

What we claim is:
1. 5-methyl-7-cyclopentyloxy-2,2-dimethyl-2H-chromene.

* * * * *